(12) United States Patent
Devic et al.

(10) Patent No.: US 8,779,217 B2
(45) Date of Patent: Jul. 15, 2014

(54) METHOD FOR PREPARING FLUORINE COMPOUNDS

(75) Inventors: Michel Devic, Sainte Foy Les Lyon (FR); Nicolas Doucet, Lyons (FR); Laurent Wendlinger, Soucieu en Jarrest (FR); Geraldine Cavallini, Saint-Symphorien d'Ozon (FR); Pierre-Marie Sedat, Fleurieux sur l'Arbresle (FR); Karine Avril, Lyons (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/382,574

(22) PCT Filed: May 21, 2010

(86) PCT No.: PCT/FR2010/050990
§ 371 (c)(1),
(2), (4) Date: Jan. 31, 2012

(87) PCT Pub. No.: WO2011/010024
PCT Pub. Date: Jan. 27, 2011

(65) Prior Publication Data
US 2012/0136183 A1 May 31, 2012

(30) Foreign Application Priority Data
Jul. 23, 2009 (FR) ..................................... 09 55138

(51) Int. Cl.
*C07C 17/25* (2006.01)
*C07C 17/354* (2006.01)

(52) U.S. Cl.
USPC ............................ 570/126; 570/153; 570/157

(58) Field of Classification Search
None
See application file for complete search history.

(56) References Cited

U.S. PATENT DOCUMENTS

| | | | |
|---|---|---|---|
| 3,882,014 A * | 5/1975 | Monday et al. ............... | 208/134 |
| 4,414,185 A * | 11/1983 | Harrison ....................... | 423/163 |
| 5,396,000 A | 3/1995 | Nappa et al. | |
| 5,679,825 A | 10/1997 | Ooms et al. | |
| 2005/0090698 A1 | 4/2005 | Merbel et al. | |
| 2009/0131727 A1 * | 5/2009 | Yang et al. .................... | 570/175 |
| 2010/0121115 A1 | 5/2010 | Rao et al. | |
| 2010/0145111 A1 | 6/2010 | Sharratt et al. | |
| 2010/0185029 A1 | 7/2010 | El Sheikh et al. | |
| 2010/0305370 A1 | 12/2010 | Devic et al. | |
| 2011/0112338 A1 | 5/2011 | Smith et al. | |
| 2011/0190554 A1 | 8/2011 | Pigamo et al. | |

FOREIGN PATENT DOCUMENTS

| | | |
|---|---|---|
| WO | WO 2008/030440 A2 | 3/2008 |
| WO | WO 2008/057794 A1 | 5/2008 |
| WO | WO 2008075017 A2 * | 6/2008 |
| WO | WO 2009/084703 A1 | 7/2009 |
| WO | WO 2009138764 A1 * | 11/2009 |

OTHER PUBLICATIONS

Knunyants, I.L., et al., XP 000578879—Reactions of Fluoro Olefins—Communication 13—Catalytic Hydrogenation of Perfluoro Olefins. pp. 1312-1317 Academy of Sciences of the USSR, Aug. 1960.
Sianesi, Dario XP009092725 Fluoroolefine—Nota I. Cis e trans 1,2,3,3,3—Pentafluoropropilence. pp. 850-861, Apr. 26, 1965.

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

The invention relates to a method for preparing fluoropropenes of formula (I) $CF_3CF=CHR$, where R is a hydrogen or a fluorine atom from at least one compound of formula (Ia) $CF_3CF=CFR$, where R has the same meaning as in formula (I), said method including the following steps: (i) hydrogenating at least one compound of formula (Ia) in an adiabatic reactor in the presence of a catalyst with a superstoichiometric amount of hydrogen so as to produce a hydrofluoropropane; (ii) partially condensing the flow from the adiabatic reactor of step (i) so as to produce a gaseous phase fraction, including unreacted hydrogen and a portion of the formed hydrofluoropropane, which is recirculated to step (i), and a liquid phase fraction including the residue of the hydrofluoropropane; (iii) dehydrofluorinating hydrofluoropropane from the liquid fraction of step (ii) using potassium hydroxide in an aqueous reaction medium contained in an agitated reactor so as to produce the fluoropropene of formula (I); and (iv) purifying the fluoropropene obtained in step (iii).

17 Claims, No Drawings

METHOD FOR PREPARING FLUORINE COMPOUNDS

FIELD OF THE INVENTION

A subject-matter of the invention is a process for the preparation of fluoroolefin compounds.

BACKGROUND OF THE INVENTION

Hydrofluorocarbons (HFCs) and in particular hydrofluoroolefins, such as 2,3,3,3-tetrafluoro-1-propene (HFO-1234yf), are compounds known for their properties of refrigerants and heat-transfer fluids, extinguishers, propellants, foaming agents, blowing agents, gaseous dielectrics, monomer or polymerization medium, support fluids, agents for abrasives, drying agents and fluids fir energy production units. Unlike CFCs (chlorofluorocarbons)and HCFCs (hydrochlorofluorocarbons), which are potentially dangerous to the ozone layer, HFOs do not comprise chlorine and thus do not present a problem for the ozone layer.

1,2,3,3,3-Pentafluoropropene (HFO-1225ye) is a synthetic intermediate in the manufacture of 2,3,3,3-tetrafluoro-1-propene (HFO-1234yf).

Several processes for the manufacture of fluoroolefin compounds are known.

The document Knunyants et al., Journal of the USSR Academy of Sciences, Chemistry Department, "Reactions of fluoro-olefins", Report 13, "Catalytic hydrogenation of perfluoro-olefins", 1960, clearly describes various chemical reactions on fluorinated compounds. This document describes the substantially quantitative hydrogenation of hexafluoropropene (HFP) over a catalyst based on palladium supported on alumina, the temperature changing from 20° C. to 50° C. and then being maintained at this value, This document describes the dehydrofluorination of 1,1,1,2,3,3-hexafluoropropane (HFC-236ea) by passing through a suspension of KOH in dibutyl ether, in order to produce 1,2,3,3,3-pentafluoro-1-propene (HFO-1225ye) with a yield of only 60%. This document describes the hydrogenation of 1,2,3,3,3-pentafluoro-1-propene (HFO-1225ye) to give 1,1,1,2,3-pentafluoropropane (HFC-245eb) over a catalyst formed of palladium supported on alumina. During this hydrogenation, a hydrogenolysis reaction also takes place, a significant amount of 1,1,1,2-tetrafluoropropane being produced. This document describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether, with a yield of only 70%. These reactions are described independently of one another even if it is indicated that it is possible to combine them in order to synthesize a range of ethylene, propylene and isobutylene derivatives comprising variable amounts of fluorine.

The document U.S. Pat. No. 5,396,000 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225)re), followed by a hydrogenation in order to produce the desired compound. The dehydrohalogenation of HFC-236ea to give HFO-1225ye is carried out in the gas phase, the reaction product being, in one example, conveyed directly to the following reactor in which the hydrogenation of the compound HFO-1225ye to give the compound HFC-245eb takes place. It is also indicated in this document that the compound HFC-236ea can be obtained by hydrogenation of hexafluoropropylene (HFP).

The document U.S. Pat. No. 5,679,875 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225ye), followed by hydrogenation to produce the desired compound. The reactions are carried out in the gas phase. It is also indicated in this document that the compound HFC-236ea can be obtained by hydrogenation of hexafluoropropylene (HFP).

The document WO 2008/030440 describes the preparation of HFO-1234yf from HFO-1225ye by reacting HFO-1225ye with hydrogen in the presence of a catalyst, in order to give HFC-245eb, and by then reacting the HFC-245eb either with a basic aqueous solution in the presence of a phase transfer catalyst and a non-aqueous and non-alcoholic solvent or in the gas phase in the presence of a catalyst. The hydrogenation reaction can be carried out at a temperature of between 50 and 300° C. or between 50 and 200° C.

The document WO 2008/030440 suggests the use of a tubular reactor for the stage of hydrogenation of HFO-1225ye, This document is completely silent with regard to the exothermicity of the hydrogenation reaction or the lifetime of the catalyst.

The document WO 2008/057794 describes a process for the manufacture of fluoroolefin compounds having from three to six carbon atoms and a degree of halogen substitution N comprising (i) the conversion, in at least two reaction stages, of a fluoroolefin starting material having the same carbon number as the desired fluoroolefin compound but a degree of halogen substitution N+1, to give a fluoroalkane having a degree of halogen substitution N+1, and (ii) the conversion of the fluoroalkane produced in (i) to give desired fluoroolefin compounds.

According to the document WO 2008/057794, the purpose of the use of several stages for the conversion (i) to give the fluoroalkane is to increase the conversion and the selectivity.

Table 1 of this document illustrates the conversion (i) in at least four stages with different temperatures and different amounts of catalyst for each stage.

The conversion (i) in several stages of the document WO 2008/057794 is not easy to implement on the industrial scale.

There exists a need for an integrated process for the preparation of fluoroolefin compounds, the use of which on the industrial scale is easier and/or more reliable, while making it possible to obtain fluoroolefin. compounds of high purity with a good yield.

DETAILED DESCRIPTION OF THE INVENTION

The invention thus provides a process for the preparation of fluoropropenes of formula (I) $CF_3CF=CHR$, in which R represents a hydrogen atom or a fluorine atom, from at least one compound of formula (Ia) $CF_3CF=CFR$, in which R has the same meanings as in the formula (I), comprising the following stages:

(i) hydrogenation, in an adiabatic reactor in the presence of a catalyst, of at least one compound of formula (Ia) with hydrogen in a superstoichiometric amount, to give at least one hydrofluoropropane;

(ii) partial condensation of the stream resulting from the adiabatic reactor of stage (i) to give a gas-phase fraction, comprising unreacted hydrogen and a portion of hydrofluoropropane formed in stage (i), which is recycled to the hydrogenation stage, and a liquid-phase fraction comprising the remaining hydrofluoropropane formed in (i);

(iii) dehydrofluorination of the hydrofluoropropane originating from the liquid fraction of stage (ii) using potassium hydroxide (KOH) in an aqueous reaction medium present in a stirred reactor, to give the fluoropropene of formula (I); and (iv) purification of the fluoropropene of formula (I).

The process according to the present invention can additionally comprise;

a stage of treatment of the potassium salt coproduced in the dehydrofluorination stage (iii) to regenerate the potassium hydroxide, a stage of heating the gas stream recycled to the adiabatic reactor.

According to one embodiment of the present invention, 1,2,3,3,3-pentafluoropropene is obtained from hexafluoropropene.

According to another embodiment of the present invention, 2,3,3,3-tetrafluoro-1-propene is obtained from 1,2,3,3,3-pentafluoropropene.

The process according to the present invention can be carried out batchwise, semicontinuously or continuously. Advantageously, the process is carried out continuously.

The Applicant Company has found that the recycling of a portion of hydrofluoropropane formed in (i) makes it possible to control the high exothermicity of the hydrogenation reaction of stage (i) and thus to improve the lifetime of the catalyst. In addition, the partial condensation of stage (ii) makes it possible to avoid the entrainment of the hydrogen in the subsequent stages, thus facilitating the recovery of the high-purity fluoropropene with a good yield.

Hydrogenation Stage (i)

The hydrogenation stage can be carried out in the presence of an $H_2$/compound of formula (Ia) molar ratio of between 1.1 and 40, preferably of between 2 and 15.

The hydrogenation stage can be carried out at a pressure of between 0.5 and 20 bar absolute and preferably between 1 and 5 bar absolute.

Mention may in particular be made, as catalysts capable of being used in the hydrogenation stage, of catalysts based on a metal from Group VIII or rhenium which is optionally supported, for example on carbon, silicon carbide, alumina or aluminium fluoride.

Use may be made, as metal, of platinum or palladium, in particular palladium, advantageously supported on carbon or alumina. It is also possible to combine this metal with another metal, such as silver, copper, gold, tellurium, zinc, chromium, molybdenum and thallium.

The catalyst can be present in any appropriate form, extrudates, pellets or beads.

Preferably, use is made of a catalyst comprising between 0.05 and 10% by weight and advantageously between 0.1 and 5% by weight of palladium supported on alumina or carbon.

The hydrogenation stage can be carried out under conditions such that the temperature at the inlet of the adiabatic reactor is between 30 and 200° C., preferably between 40 and 140° C., and the temperature at the outlet of the adiabatic reactor is between 50 and 250° C., preferably between 80 and 160° C.

The contact time (ratio of the volume of catalyst to the total gas stream under standard temperature and pressure conditions) is preferably between 0.2 and 10 seconds and advantageously between 1 and 5 seconds.

This hydrogenation stage can be carried out in a multistage adiabatic reactor.

The stage of hydrogenation of the compound of formula (Ia) is substantially quantitative.

Condensation Stage (ii)

The stream on conclusion of the hydrogenation stage (i) is subjected to a condensation stage under conditions such that the unreacted hydrogen is not condensed and that a portion of hydrofluoroalkane formed in stage (i) is condensed.

Preferably, the condensation stage is carried out at a temperature of between 0 and 50° C. and at a pressure of between 0.5 and 20 bar absolute, advantageously between 1 and 5 bar absolute.

Preferably, the condensation stage is carried out under conditions such that between 1 and 30% of the hydrofluoroalkane at the outlet of the reactor in stage (i) is condensed and advantageously between 2 and 10% is condensed.

The noncondensed fraction is subsequently recycled to the hydrogenation stage (i) after optionally being heated.

Dehydrofluorination Stage (iii)

The condensed fraction comprising hydrofluoropropane, after evaporation, is subsequently subjected to a dehydrofluorination stage using potassium hydroxide present in an amount preferably of between 20 and 75% by weight and advantageously of between 55 and 70% by weight, with respect to the weight of the water and KOH mixture of the aqueous reaction medium present in the stirred reactor.

The aqueous reaction medium of the dehydrofluorination stage is preferably maintained at a temperature of between 80 and 180° C., advantageously of between 125 and 180° C. A particularly preferred temperature of the reaction medium is between 145 and 165° C.

The dehydrofluorination stage can be carried out at a pressure of 0.5 to 20 bar but it is preferable to operate at a pressure of between 0.5 and 5 bar absolute and more advantageously between 1.1 and 2.5 bar absolute.

When the compound to be hydrogenated is hexafluoropropene, the dehydrofluorination stage consists in reacting 1,1,1,2,3,3-hexafluoropropane (HFC-236ea) with potassium hydroxide to give 1,2,3,3,3-pentafluoropropene.

When the compound to be hydrogenated is 1,2,3,3,3-pentafluoropropene, the dehydrofluorination stage consists in reacting 1,1,1,2,3-pentafluoropropane (HFC-245eb) with potassium hydroxide to give 2,3,3,3-tetrafluoropropene.

Treatment Stage to Regenerate the Potassium Hydroxide

Potassium fluoride is formed during the dehydrofluorination stage.

The process according to the present invention can comprise a treatment stage during Which the potassium fluoride coproduced in the dehydrofluorination stage is brought into contact with calcium hydroxide in an aqueous reaction medium at a temperature preferably of between 50 and 150° C., advantageously of between 70 and 120° C. and more advantageously of between 70 and 100° C.

This treatment stage is preferably carried out by introducing calcium hydroxide into a reactor comprising a portion of the reaction medium originating from the dehydrofluorination stage which comprises potassium fluoride, potassium hydroxide and water, after optional dilution.

The potassium fluoride is preferably present at between 4 and 45% by weight, with respect to the reaction medium originating from the dehydrofluorination stage (iii).

The reaction medium of the treatment preferably comprises between 4 and 50% by weight of potassium hydroxide and advantageously between 10 and 35% by weight of potassium hydroxide, with respect to the total weight of potassium hydroxide and water in the medium.

The stage of treatment with calcium hydroxide makes it possible to regenerate potassium hydroxide, which can be recycled to the dehydrofluorination stage, and to obtain calcium fluoride of commercial quality, which can be recovered in value after separation, for example by filtration and settling.

Calcium fluoride with a mean size of between 20 and 35 μm (mean size at 50% by weight of the particle size distribution) is obtained under the preferred conditions of this treatment stage.

The stage of treatment with calcium hydroxide can be carried out in any type of reactor known to a person skilled in the art, for example a stirred reactor.

Stage of Purification of the Fluoropropene of Formula (I)

The gas stream on conclusion of the dehydrofluorination stage (iii), comprising the fluoropropene of formula (I), the unreacted compound of formula (Ia) and the by-products, is subjected to a purification stage in order to obtain high-purity fluoropropenes.

The purification preferably comprises a first distillation stage, in order to separate the light impurities, and a second distillation stage, in order to separate the fluoropropene of formula (I) from the heavy impurities.

In the absence of the condensation stage (ii), hydrogen is encountered in the light impurities of the first distillation stage.

When the desired product is 1,2,3,3,3-pentafluoropropene, the light impurities to be removed comprise trifluoroethylene.

When the desired product is 2,3,3,3-tetrafluoropropene, the light impurities to be removed comprise trifluoropropyne.

When the desired product is 1,2,3,3,3-pentafluoropropene, the heavy impurities to be removed comprise 1,1,1,2,3,3-hexafluoropropane (HFC-236ea), which can be recycled to stage (iii).

When the desired product is 2,3,3,3-tetrafluoropropene, the heavy impurities to be removed comprise 1,1,1,2,3-pentafluoropropane (HFC-245eb) which can be recycled to stage (iii).

It should be remembered that:
the degree of conversion is the % of the starting material which has reacted (number of moles of starting material which has reacted/number of moles of starting material introduced);
the selectivity for the desired product is the number of moles of desired product formed/number of moles of starting material Which has reacted ratio.

EXAMPLE

The following example illustrates the invention without limiting it.

Synthesis of HFO-1225ye by hydrogenation of HFP to give HFC-236ea, followed by dehydrofluorination of the HFC-236ea to give HFO-1225ye.

Hydrogenation of HFP to Give HFC-236ea

Use is made of a tubular reactor made of stainless steel, with an internal diameter of 2.1 cm and a length of 120 cm, containing 479 g, i.e. 330 cm$^3$, of catalyst in the form of a fixed bed. The catalyst comprises 0.2% by weight of palladium supported on α-alumina.

Throughout the duration of the reaction, approximately 0.71 mol/h of hydrogen and 0.7 mol/h of hexafluoropropene are continuously injected. The pressure is 2 bar absolute. The hydrogen/HFP molar ratio at the inlet of the reactor is 6. The temperature at the inlet of the reactor is 43.2° C. and the maximum temperature achieved during the reaction is 122.3° C. The contact time according to the definition given above is 2.8 s.

An HFP conversion of 100% is obtained with a selectivity for HFC-236ea of greater than 99%.

The stream at the outlet of the reactor is cooled to 17.6° C. and partially condensed. The gas phase is recycled to the reactor after having been preheated beforehand. The liquid phase, representing 5% of the HFC-236ea present at the outlet of the reactor, is composed of HFC-236ea to more than 99%. It is evaporated before feeding the dehydrofluorination reactor.

Dehydrofluorination of the HFC-236ea to Give FIFO-1225ye

Use is made of a stirred 3 liter reactor made of stainless steel with an internal diameter of 1.5 cm which contains 2.6 liters of an approximately 60% by weight potassium hydroxide solution.

Throughout the duration of the reaction, approximately 0.7 mol/h of HFC-236ea gas and approximately 6.4 mol/h of a liquid solution of potassium hydroxide comprising approximately 70% by weight of KOH (i.e., 2.7 moll of pure KOH) are continuously injected. The pressure is 1.1 bar absolute.

The temperature at the inlet of the reactor is 160° C.

An HFC-236ea conversion of 98% is obtained with a selectivity for HFO-1225ye (E+Z) of greater than 99%. The purity of the HFO-1225ye (E+Z) is greater than 97%.

The invention claimed is:

1. Process for the preparation of fluoropropenes of formula (I) CF$_3$CF=CHR, in which R represents a hydrogen atom or a fluorine atom, from at least one compound of formula (Ia) CF$_3$CF=CFR, comprising the following steps:
    (i) hydrogenating, in an adiabatic reactor in the presence of a catalyst, at least one compound of formula CF$_3$CF=CFR (Ia) with hydrogen in a superstoichiometric amount, to produce a stream comprising at least one hydrofluoropropane;
    (ii) partially condensing the stream to give a gas-phase fraction and a liquid-phase fraction, the gas-phase fraction comprising unreacted hydrogen and a first portion of hydrofluoropropane formed in step (i), and the liquid-phase fraction comprising a second portion of hydrofluoropropane formed in step (i), wherein the partial condensation is carried out at a temperature of between 0 and 50° C. and at a pressure of between 0.5 and 20 bar absolute such that the unreacted hydrogen is not condensed, and wherein said gas-phase fraction is recycled to step (i);
    (iii) dehydrofluorinating the second portion of hydrofluoropropane in an aqueous reaction medium comprising potassium hydroxide in a stirred reactor, to give a fluoropropene of formula (I) CF$_3$CF=CHR and potassium fluoride (KF); and
    (iv) purifying the fluoropropene of formula (I) CF$_3$CF=CHR.

2. The process according to claim 1, in which the hydrogen/compound of formula (Ia) molar ratio is between 1.1 and 40.

3. The process according to claim 1, in which the temperature at the inlet of the adiabatic reactor of step (i) is between 30 and 200° C., and the temperature at the outlet of the adiabatic reactor is between 50 and 250° C.

4. The process according to claim 1, characterized in that the pressure of the adiabatic reactor is between 0.5 and 20 bar absolute.

5. The process according to claim 1, characterized in that the potassium hydroxide represents between 20 and 75% by weight, of the aqueous reaction mixture of step (iii).

6. The process according to claim 1, characterized in that the aqueous reaction mixture of step (iii) is at a temperature of between 125 and 180° C.

7. The process according to claim 1, characterized in that it further comprises a treatment step comprising reacting the potassium fluoride with calcium hydroxide to produce potassium hydroxide.

8. The process according to claim 7, characterized in that the potassium hydroxide represents between 4 and 50% by weight, with respect to the total weight of potassium hydroxide and water of the aqueous reaction medium.

9. The process according to claim 7, characterized in that the treatment temperature is between 50 and 150° C.

10. The process according to claim 1, characterized in that the purification of step (iv) comprises a first distillation, to remove light impurities, and a second distillation, to remove heavy impurities.

11. The process according to claim 1, characterized in that said compound of formula (Ia) comprises hexafluoropropene, said hydrofluoropropane comprises 1,1,1,2,3,3-hexafluoropropene, and said fluoropropene comprises 1,2,3,3,3-pentafluoropropene.

12. The process according to claim 1, characterized in that said compound of formula (Ia) comprises 1,2,3,3,3-pentafluoropropene and said hydrofluoropropane comprises 1,1,1,2,3-pentafluoropropane, and said fluoropropene comprises 2,3,3,3-tetrafluoropropene.

13. The process according to claim 1, in which the hydrogen/compound of formula (Ia) molar ratio is between 2 and 15.

14. The process according to claim 1, in which the temperature at the inlet of the adiabatic reactor of step (i) is between 40 and 140° C., and the temperature at the outlet of the adiabatic reactor is between 80 and 160° C.

15. The process according to claim 1, characterized in that the pressure of the adiabatic reactor is between 1 and 5 bar absolute.

16. The process according to claim 1, characterized in that the partial condensation step (ii) is carried out at a pressure of between 1 and 5 bar absolute.

17. The process according to claim 1, characterized in that the aqueous reaction mixture of step (iii) is at a temperature of between 145 and 165° C.

* * * * *

UNITED STATES PATENT AND TRADEMARK OFFICE
CERTIFICATE OF CORRECTION

PATENT NO. : 8,779,217 B2  
APPLICATION NO. : 13/382574  
DATED : July 15, 2014  
INVENTOR(S) : Devic et al.

Page 1 of 1

It is certified that error appears in the above-identified patent and that said Letters Patent is hereby corrected as shown below:

On the Title Page

Item [75]: Please delete "Nicolas Doucet, Lyons (FR)" and insert --Nicolas Doucet, Lyon (FR)--;

Item [75]: Please delete "Karine Avril, Lyons (FR)" and insert --Karine Avril, Lyon (FR)--;

In the Claims

Column 6, Claim 1, line 1, please delete "Process for the preparation" and insert --A process for the preparation--; and Column 7, Claim 11, lines 3-4, please delete "1,1,1,2,3,3-hexafluoropropene" and insert --1,1,1,2,3,3-hexafluoropropane--.

Signed and Sealed this  
Seventh Day of October, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,779,217 B2  
APPLICATION NO. : 13/382574  
DATED : July 15, 2014  
INVENTOR(S) : Devic et al.

Page 1 of 1

It is certified that error appears in the above-identified patent and that said Letters Patent is hereby corrected as shown below:

On the Title Page

Item [75]: Please delete "Nicolas Doucet, Lyons (FR)" and insert --Nicolas Doucet, Lyon (FR)--;

Item [75]: Please delete "Karine Avril, Lyons (FR)" and insert --Karine Avril, Lyon (FR)--;

In the Claims

Column 6, Claim 1, line 20, please delete "Process for the preparation" and insert --A process for the preparation--; and Column 7, Claim 11, lines 11-12, please delete "1,1,1,2,3,3-hexafluoropropene" and insert --1,1,1,2,3,3-hexafluoropropane--.

This certificate supersedes the Certificate of Correction issued October 7, 2014.

Signed and Sealed this  
Eleventh Day of November, 2014

Michelle K. Lee  
*Deputy Director of the United States Patent and Trademark Office*